United States Patent
Onodera et al.

(10) Patent No.: US 11,767,441 B2
(45) Date of Patent: Sep. 26, 2023

(54) COSMETIC INK, INK JET INK AND INK CARTRIDGE INCLUDING THE SAME, AND METHOD FOR PRODUCING COSMETIC SHEET

(71) Applicant: Panasonic Intellectual Property Management Co., Ltd., Osaka (JP)

(72) Inventors: Mari Onodera, Osaka (JP); Masayo Shinoda, Tokyo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 43 days.

(21) Appl. No.: 16/819,029

(22) Filed: Mar. 13, 2020

(65) Prior Publication Data

US 2020/0216693 A1 Jul. 9, 2020

Related U.S. Application Data

(63) Continuation of application No. PCT/JP2018/033901, filed on Sep. 13, 2018.

(30) Foreign Application Priority Data

Oct. 10, 2017 (JP) ................. 2017-197067

(51) Int. Cl.
| | |
|---|---|
| C09D 11/32 | (2014.01) |
| A61K 8/02 | (2006.01) |
| A61K 8/04 | (2006.01) |
| A61Q 1/02 | (2006.01) |
| B41J 2/21 | (2006.01) |

(52) U.S. Cl.
CPC ............ *C09D 11/32* (2013.01); *A61K 8/0241* (2013.01); *A61K 8/04* (2013.01); *A61Q 1/02* (2013.01); *B41J 2/21* (2013.01); *A61K 2800/87* (2013.01)

(58) Field of Classification Search
None
See application file for complete search history.

(56) References Cited

U.S. PATENT DOCUMENTS

| | | | | |
|---|---|---|---|---|
| 2001/0019682 | A1 | 9/2001 | Sukhna et al. | |
| 2004/0233262 | A1* | 11/2004 | Randler | C09D 11/32 |
| | | | | 347/100 |
| 2005/0002881 | A1* | 1/2005 | Aota | A61K 8/40 |
| | | | | 424/63 |
| 2007/0183998 | A1* | 8/2007 | Suzuki | A61Q 1/12 |
| | | | | 424/63 |
| 2011/0236332 | A1* | 9/2011 | Dop | A61Q 1/06 |
| | | | | 132/317 |
| 2014/0017288 | A1* | 1/2014 | Matsushita | A61K 8/19 |
| | | | | 424/59 |
| 2015/0265030 | A1 | 9/2015 | Kusukame et al. | |
| 2015/0297471 | A1 | 10/2015 | Sunkel et al. | |
| 2015/0342845 | A1 | 12/2015 | Hwang et al. | |
| 2015/0359712 | A1* | 12/2015 | Rabe | B41J 2/14016 |
| | | | | 347/9 |
| 2016/0367460 | A1* | 12/2016 | Handley | D06M 11/58 |
| 2017/0073535 | A1 | 3/2017 | Kusukame et al. | |
| 2020/0215356 | A1 | 7/2020 | Onodera et al. | |

FOREIGN PATENT DOCUMENTS

| | | | |
|---|---|---|---|
| CN | 104921959 | A | 9/2015 |
| CN | 106519789 | A | 3/2017 |
| JP | 59-162055 | | 9/1984 |
| JP | 61-281171 | A | 12/1986 |
| JP | 10-042950 | | 2/1998 |
| JP | 2003-511281 | | 3/2003 |
| JP | 2011-194887 | | 10/2011 |
| JP | 2015-043836 | | 3/2015 |
| JP | 2015-193604 | | 11/2015 |
| JP | 2017-518091 | | 7/2017 |
| WO | WO 2015/161009 | * | 10/2015 |
| WO | 2019/073626 | A1 | 4/2019 |

OTHER PUBLICATIONS

Extended European Search Report dated Aug. 26, 2020 issued in European Patent Application No. 18865837.1.
International Search Report of PCT application No. PCT/JP2018/033901 dated Dec. 18, 2018.
English Translation of Chinese Search Report dated Mar. 30, 2022 for Chinese Patent Application No. 201880064777.0.

* cited by examiner

*Primary Examiner* — David J Blanchard
*Assistant Examiner* — Sarah J Chickos
(74) *Attorney, Agent, or Firm* — GREENBLUM & BERNSTEIN, P.L.C.

(57) ABSTRACT

A cosmetic ink includes a colorant, a higher alcohol having 3 or more carbon atoms, purified water, an acrylic-based resin, and a film-forming agent. The colorant includes a white-based pigment, a yellow-based pigment, a red-based pigment, and a blue-based pigment. In a coating film of the cosmetic ink, a spectral reflectance curve obtained by measuring spectral reflectances in wavelengths of 400 nm to 700 nm has a first inflection point in a wavelength region of 550 nm or more and 610 nm or less, and a second inflection point in a wavelength region of less than 550 nm; a spectral reflectance at the first inflection point is higher than a spectral reflectance at the second inflection point; and spectral reflectances throughout a wavelength region of more than 580 nm are equal to or higher than a spectral reflectance at a wavelength of 580 nm.

12 Claims, 5 Drawing Sheets

COSMETIC INK, INK JET INK AND INK CARTRIDGE INCLUDING THE SAME, AND METHOD FOR PRODUCING COSMETIC SHEET

BACKGROUND

1. Technical Field

The present disclosure relates to a cosmetic ink, an ink jet ink and an ink cartridge that include the cosmetic ink, and a method for producing a cosmetic sheet.

2. Description of the Related Art

It has been proposed that nanosheets coated with inks including various colorants are affixed to the human body, to thereby make blotches, birthmarks, scars (hereafter, also referred to as "discolored area") and the like on the skin less noticeable (for example, Japanese Unexamined Patent Application Publication No. 2015-43836). According to the technique of Japanese Unexamined Patent Application Publication No. 2015-43836, the skin is photographed and a discolored area is identified. A nanosheet is processed by printing so as to have a color close to the color of the outside area of the discolored area, and affixed to the skin, to thereby make the discolored area less noticeable.

SUMMARY

However, in the case of using existing cosmetic sheets, it is difficult to reproduce the color of the skin. In particular, in masking of the discolored area, the larger the amount of ink applied, the larger the difference from the original skin color in the sheet affixed.

In one general aspect, the techniques disclosed here feature a cosmetic ink including: (A) a colorant including a white-based pigment, a yellow-based pigment, a red-based pigment, and a blue-based pigment; (B) a higher alcohol having 3 or more carbon atoms; (C) purified water; (D) an acrylic-based resin including at least one polymer selected from the group consisting of a homopolymer of an acrylic-based monomer and a copolymer of two or more acrylic-based monomer species; and (E) a film-forming agent, wherein a spectral reflectance curve obtained by measuring spectral reflectances in wavelengths of 400 nm to 700 nm of a coating film of the cosmetic ink has a first inflection point in a wavelength region of 550 nm or more and 610 nm or less, and a second inflection point in a wavelength region of less than 550 nm, a spectral reflectance at the first inflection point is higher than a spectral reflectance at the second inflection point, and spectral reflectances throughout a wavelength region of more than 580 nm are equal to or higher than a spectral reflectance at a wavelength of 580 nm.

An embodiment of the present disclosure provides a cosmetic ink that enables reproduction of a color close to the color of the skin irrespective of the amount of ink applied.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

1. Cosmetic Ink

A cosmetic ink according to the present disclosure is an ink for producing a cosmetic sheet. The cosmetic sheet produced using the ink is used by, for example, affixing to the skin in order to, for example, color or beautify the skin. However, the cosmetic ink is applicable not only to cosmetic applications such as making up, but also to skin care applications such as prevention from sunburn, medical applications, and industrial applications such as decoration of plastic films.

Figure 1:
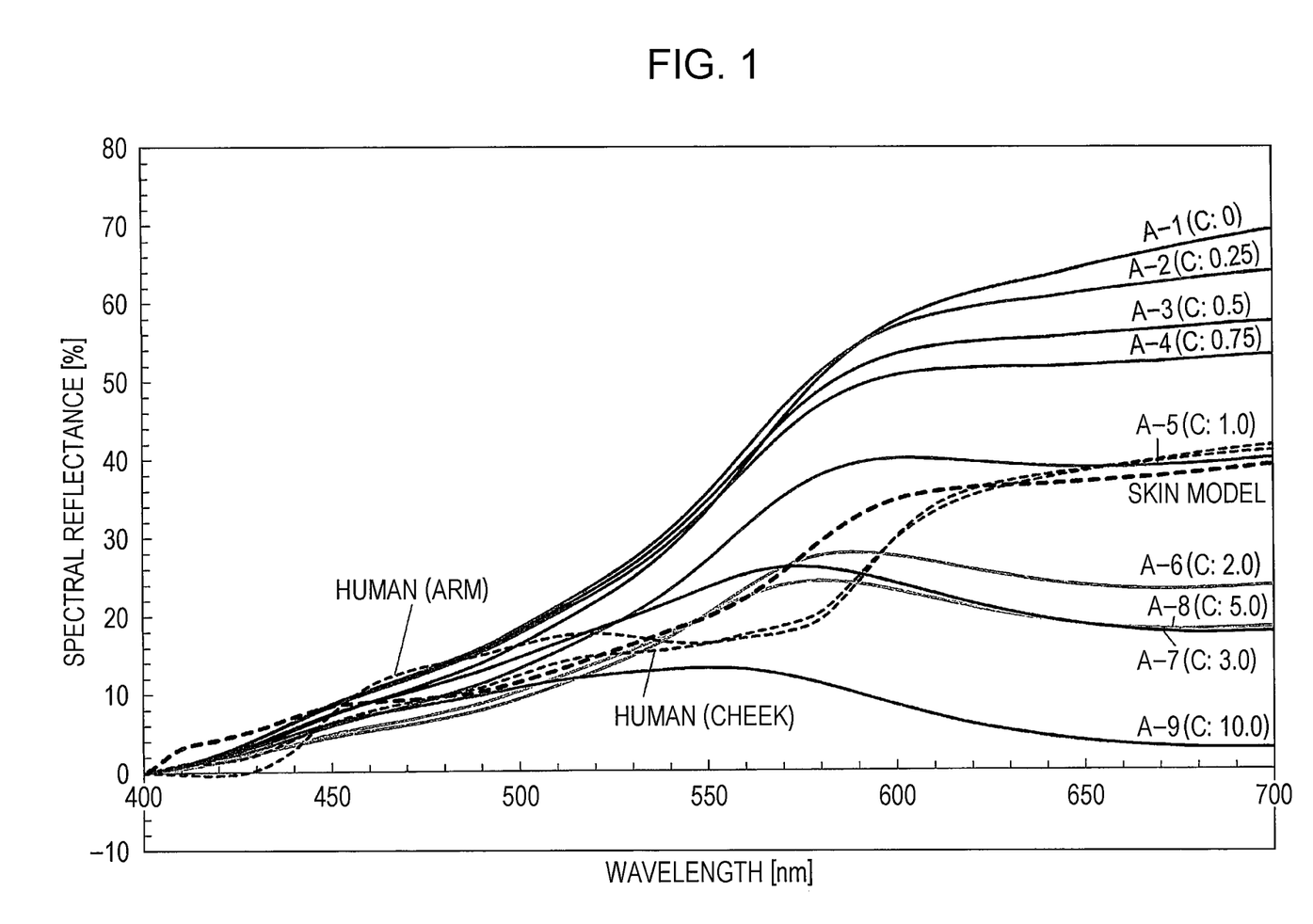
FIG. 1 is a graph of spectral reflectance curves in wavelengths of 400 nm to 700 nm of cosmetic inks of Examples according to the present disclosure and cosmetic inks of Comparative Examples.
Figure 2:
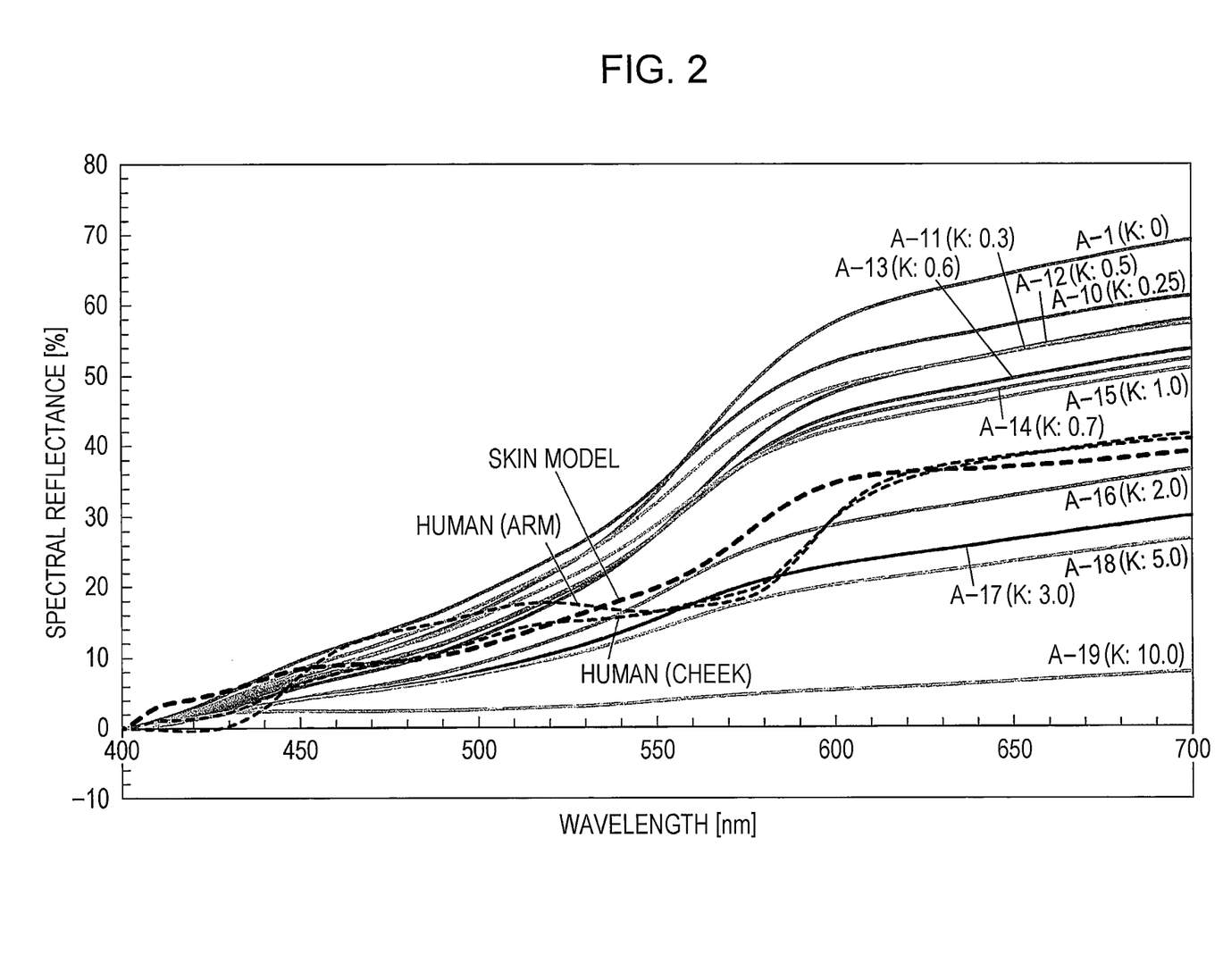
FIG. 2 is a graph of spectral reflectance curves in wavelengths of 400 nm to 700 nm of cosmetic inks of Examples according to the present disclosure and cosmetic inks of Comparative Examples.

A cosmetic ink according to the present disclosure is an ink that enables reproduction of the color of the human skin (in the present disclosure, "the color of the human skin" means the color of the Mongoloid skin unless otherwise specified), and provides a coating film having a spectral reflectance curve having a unique profile. Regarding such cosmetic inks according to the present disclosure, examples of spectral reflectances measured in wavelengths of 400 nm to 700 nm (spectral reflectance curves) are illustrated in FIG. 1 and FIG. 2. Incidentally, as described later in EXAMPLES in detail, A-1 to A-5 in FIG. 1 and A-1 and A-10 to A-18 in FIG. 2 correspond to spectral reflectance curves of cosmetic inks according to the present disclosure.

In the case of measuring a coating film of a cosmetic ink according to the present disclosure in terms of spectral reflectance in wavelengths of 400 nm to 700 nm, the spectral reflectance curve has a first inflection point in a wavelength region of 550 nm or more and 610 nm or less, and a second inflection point in a wavelength region of less than 550 nm. The spectral reflectance at the first inflection point is higher than the spectral reflectance at the second inflection point. The spectral reflectances throughout a wavelength region of more than 580 nm are equal to or higher than the spectral reflectance at a wavelength of 580 nm.

Stated another way, the spectral reflectance curve of the cosmetic ink has a sigmoid shape (S shape) in which the spectral reflectance gradually increases from a short-wavelength region to a long-wavelength region. Incidentally, the gradient between the first inflection point and the second inflection point is preferably larger than the gradient in a region of longer wavelengths relative to the first inflection point, and the gradient in a region of shorter wavelengths relative to the second inflection point. The spectral reflectance curve in wavelengths of 400 nm to 700 nm preferably does not have any inflection point other than the first inflection point and the second inflection point. In this Description, "inflection point" means a point at which the sign of the curvature of the curve changes. As the spectral reflectances of a coating film of a cosmetic ink, for example, values determined in the following manner can be employed: the cosmetic ink is applied onto a transparent substrate, and the coating film is dried and measured in terms of spectral reflectances using a spectrophotometer (such as CM-700d manufactured by KONICA MINOLTA JAPAN, INC.) with a main light source of D50 and a measurement mode of SCE.

When coating films of a cosmetic ink have the above-described spectral reflectances, coating films formed by applying large amounts of the cosmetic ink and coating films formed by applying small amounts of the cosmetic ink enable reproduction of a color close to that of the human skin. Thus, affixation of a cosmetic sheet coated with the cosmetic ink to the skin enables a reduction in the color difference from the skin. Incidentally, the spectral reflectances of a coating film of the cosmetic ink can be adjusted by, for example, changing the combination in the (A) colorant described later.

From the viewpoint of suppressing redness and providing a color close to the color of the actual human skin, a cosmetic ink according to the present disclosure preferably provides a coating film that does not have excessively high spectral reflectances in the wavelength region of 590 to 700 nm. Specifically, the spectral reflectances in the wavelength region of 590 to 700 nm are preferably in the range of 1 to 1.3 times, more preferably in the range of 1 to 1.2 times, the spectral reflectance at the wavelength of 580 nm. When a cosmetic ink provides a coating film in which the spectral reflectances in the wavelength region of 590 to 700 nm satisfy such a range, it provides a cosmetic sheet having a color closer to the color of the human skin, and achieving a reduction in the color difference between the coating film and the skin color irrespective of an increase or decrease in the amount of the ink applied. The spectral reflectances of the coating film in the wavelength region of 590 to 700 nm can be adjusted by, for example, changing the amount of a blue-based colorant in the (A) colorant described later.

On the other hand, by adjusting the lightness of the cosmetic ink, the color of the cosmetic ink (also the color of the cosmetic sheet to be provided) can also be made close to the color of the human skin. Specifically, a cosmetic ink preferably provides a coating film having, in the L*a*b* color system (CIE 1976), an L* value of 48 to 80, preferably 48 to 73. The lightness (L* value) can be measured in the following manner, for example: the cosmetic ink is applied onto a transparent substrate, and the coating film is dried and measured using a spectrophotometer (such as CM-700d manufactured by KONICA MINOLTA JAPAN, INC.) with a main light source of D50 and a measurement mode of SCE. The lightness of the coating film can be adjusted by changing the amount of a black-based colorant in the (A) colorant described later.

A cosmetic ink having the above-described spectral reflectances according to the present disclosure at least includes (A) a colorant, (B) a higher alcohol having 3 or more carbon atoms, (C) purified water, (D) an acrylic-based resin, and (E) a film-forming agent. The cosmetic ink may optionally include, in addition to the above-described components, various additives, for example. Hereinafter, components included in a cosmetic ink according to the present disclosure will be described in detail.

(A) Colorant

The (A) colorant included in the cosmetic ink is not particularly limited as long as the above-described spectral reflectances are achieved. Ordinarily, a plurality of colorants are used in combination. For example, a combination of at least a white-based colorant, a red-based colorant, and a yellow-based colorant tends to provide the above-described spectral reflectances. More specifically, the white-based colorant content relative to 100 parts by mass of the total amount of (A) colorant is preferably 60 to 99.8 parts by mass. The red-based colorant content relative to 100 parts by mass of the total amount of (A) colorant is preferably 0.1 to 30 parts by mass. The yellow-based colorant content relative to 100 parts by mass of the total amount of (A) colorant is preferably 0.1 to 30 parts by mass.

The (A) colorant preferably further includes a blue-based colorant. However, an excessively high content of the blue-based colorant results in an excessive decrease in the spectral reflectances in the wavelength region of more than 580 nm. Thus, the blue-based colorant content relative to 100 parts by mass of the total amount of (A) colorant is preferably 10 parts by mass or less, more preferably 0.1 to 10 parts by mass. The (A) colorant preferably further includes a black-based colorant. However, an excessively high content of the black-based colorant results in a decrease in the lightness of the cosmetic ink, which tends to result in an increase in the color difference from the color of the skin. Thus, the black-based colorant content relative to 100 parts by mass of the total amount of (A) colorant is preferably 5 parts by mass or less, more preferably 0.1 to 5 parts by mass.

The (A) colorant is not particularly limited as long as such compounds provide different colors, but is preferably selected from, from the viewpoint of skin irritation, for example, the components listed in "List of Cosmetic Ingredient Label Names" based on Japan Pharmaceutical Affairs Law, the components in compliance with EU Cosmetics Directive (Cosmetics Directive 76/768/EEC), and the components described in International Cosmetic Ingredient Dictionary and Handbook (Jan. 1, 2002, 9th edition) published by U.S. CTFA (Cosmetic, Toiletry & Fragrance Association, U.S.). The (A) colorant may be selected from publicly known inorganic pigments, organic pigments, and dyes. The (A) colorant may include, in addition to, for example, color pigments or color dyes for coloring cosmetic sheets, a pearl pigment for imparting glossiness to cosmetic sheets, a reflective material, or the like in combination with such colorants.

Examples of the white-based colorant include white pigments such as titanium oxide, zinc oxide, cerium oxide, and barium sulfate; and white body powders such as talc, muscovite, phlogopite, lepidolite, biotite, synthetic mica, cericite, synthetic cericite, kaolin, silicon carbide, bentonite, smectite, silicic anhydride, aluminum oxide, magnesium oxide, zirconium oxide, antimony oxide, diatomaceous earth, aluminum silicate, aluminum magnesium metasilicate, calcium silicate, barium silicate, magnesium silicate, calcium carbonate, magnesium carbonate, hydroxyapatite, and boron nitride.

Examples of the red-based colorant include inorganic red pigments such as iron oxide, iron hydroxide, and iron titanate; and inorganic brown-based pigments such as γ-iron oxide. Examples of the yellow-based colorant include inorganic yellow-based pigments such as yellow iron oxide and ocher.

Examples of the blue-based pigment include inorganic blue-based pigments such as Prussian blue (ferric ferrocyanide), ultramarine (ultramarine blue), lapis lazuli, mountain blue, aluminum-cobalt oxide, aluminum-zinc-cobalt oxide, silicon-cobalt oxide, silicon-zinc-cobalt oxide, cobalt pigments, smalt, cobalt blue, cobalt stannate, cobalt chromium blue, cobalt-aluminum-silicon oxide, and manganese blue; and organic pigments or dyes such as indigo, phthalocyanine, indanthrene blue, and sulfonated products of the foregoing. Examples of the black-based colorant include inorganic black pigments such as black iron oxide and carbon black.

Examples of colorants of other colors include inorganic purple pigments such as manganese violet and cobalt violet; inorganic green pigments such as chromium hydroxide, chromium oxide, cobalt oxide, and cobalt titanate; lakes formed from various tar-based pigments; lakes formed from various natural pigments; and composite synthetic resin powders formed from powders of the foregoing.

Examples of the pearl pigment include titanium oxide-coated mica, titanium oxide-coated mica, bismuth oxychloride, titanium oxide-coated bismuth oxychloride, titanium oxide-coated talc, fish scale flake, and titanium oxide-coated, colored mica.

Examples of the reflective material include glitter powders such as calcium aluminum borosilicate, titanium dioxide-coated mica, titanium dioxide-coated glass powder, titanium dioxide-coated bismuth oxychloride, titanium dioxide-coated mica, titanium dioxide-coated talc, iron oxide-coated mica, iron oxide-coated mica titanium, iron oxide-coated glass powder, Prussian blue-treated mica titanium, carmine-treated mica titanium, bismuth oxychloride, fish scale flake, polyethylene terephthalate-aluminum-epoxy laminated powder, and polyethylene terephthalate-polyolefin laminated film powder; organic low-molecular-weight powders such as N-acyllysine; natural organic powders such as silk powder and cellulose powder; metal powders such as aluminum powder, gold powder, and silver powder; composite powders such as fine-particle titanium oxide-coated mica titanium, fine-particle zinc oxide-coated mica titanium, barium sulfate-coated mica titanium, titanium oxide-containing silicon dioxide, and zinc oxide-containing silicon dioxide; kapok fiber; a polymethyl methacrylate crosspolymer; and uncrosslinked acrylic particles.

The (A) colorant may be a component soluble or insoluble in the (B) higher alcohol and (C) purified water described later. When the (A) colorant is composed of a component insoluble in the (B) higher alcohol and the like, the shape of the component is not particularly limited and may be any shape such as a spherical shape or an acicular shape. However, in the particle size distribution of this component measured by laser diffractometry, the median (D50) of the cumulative value is preferably 125 nm or more and 2 μm or less, more preferably 125 nm to 1000 nm. More preferably, the average particle size (D50) is 125 nm to 1000 nm, and a value (D90) at 90% of the cumulative value of the particle size distribution is 3000 nm or less. When the (A) colorant has, in the particle size distribution, an average particle size (D50) satisfying such a range, the cosmetic ink can be used for printing by various printing methods. Blue-based colorants and black-based colorants particularly have large color differences from the color of the skin. Thus, when the cosmetic ink includes such a black-based colorant and a blue-based colorant having large average particle sizes, the colorants in the resultant coating film tend to be recognized. By contrast, when the colorants have average particle sizes satisfying such a range, the colorants tend not to be recognized, and the resultant coating film tends to have a uniform color.

The total amount of (A) colorant included in 100 parts by mass of the cosmetic ink is preferably 3 parts by mass or more and 40 parts by mass or less, more preferably 3 to 30 parts by mass. When the total amount of (A) colorant is 3 parts by mass or more, the cosmetic sheet tends to have, for example, the color or glossiness derived from the colorant. When the amount of (A) colorant is excessively large, the (A) colorant may, for example, aggregate, so that it may become difficult to apply the cosmetic ink from various printing apparatuses. However, when the amount of (A) colorant is 40 mass % or less, the (A) colorant tends not to, for example, aggregate, so that printing can be performed with stability.

(B) Higher Alcohol

The higher alcohol included in a cosmetic ink according to the present disclosure is not particularly limited as long as it is a higher alcohol having 3 or more carbon atoms and being miscible with the (C) purified water. The (B) higher alcohol functions as a solvent of the cosmetic ink. Incidentally, after printing with the cosmetic ink on a printing medium, the (B) higher alcohol is absorbed by or evaporates from the printing medium.

The higher alcohol preferably has 3 to 5 carbon atoms, more preferably 3 or 4 carbon atoms. When the higher alcohol has carbon atoms satisfying such a range, it has higher miscibility with the (C) purified water.

The (B) higher alcohol preferably includes a trihydric alcohol. When the (B) higher alcohol includes a trihydric alcohol, the (B) higher alcohol and the (C) purified water tend not to excessively evaporate within various printing apparatuses. As a result, printing can be performed with stability using the printing apparatuses. In addition, in this case, the viscosity of the cosmetic ink is kept constant, which enables formation of desired images with stability.

In particular, the trihydric alcohol is preferably glycerol. Glycerol has high safety for living bodies. When the cosmetic ink includes glycerol, aggregation of the (A) colorant and the like tends to be suppressed, so that storage of the cosmetic ink for a long period of time tends not to cause thickening, for example.

On the other hand, the (B) higher alcohol may include a dihydric alcohol or a monohydric alcohol. Examples of the dihydric alcohol include diethylene glycol, propylene glycol, 1,3-propanediol, butylene glycol, and hexanediol. Examples of the monohydric alcohol include propanol, isopropanol, and butyl alcohol. Of these, the dihydric alcohol is preferred, in particular, propylene glycol is preferred. The dihydric alcohol has lower viscosity and lower surface tension than the (C) purified water and the trihydric alcohol. Thus, when the cosmetic ink includes the dihydric alcohol, the cosmetic ink has improved wettability over printing media, and the resultant images tend not to have unevenness.

The total amount of (B) higher alcohol included in 100 parts by mass of the cosmetic ink is preferably 20 parts by mass or less, more preferably 10 to 20 parts by mass. When the amount of (B) higher alcohol is excessively large, the (A)

colorant and the like tend to aggregate. By contrast, when the amount of higher alcohol is 20 parts by mass or less, aggregation of the (A) colorant and the like tends not to occur, so that the cosmetic ink can be ejected with stability from various printing apparatuses.

The amount of trihydric alcohol relative to 100 parts by mass of the cosmetic ink is appropriately selected in accordance with the printing method for the cosmetic ink. For example, in the case of printing with the cosmetic ink using an ink jet apparatus, the amount is preferably 20 parts by mass or less, more preferably 10 to 20 parts by mass. When the amount of trihydric alcohol satisfies such a range, in the cosmetic ink, evaporation properties of the (B) higher alcohol and the (C) purified water are appropriately adjusted, so that the cosmetic ink can be ejected from an ink jet apparatus with stability.

The amount of dihydric alcohol relative to 100 parts by mass of the cosmetic ink is also appropriately selected in accordance with the printing method for the cosmetic ink. For example, in the case of printing with the cosmetic ink using an ink jet apparatus, the amount is preferably 20 parts by mass or less, more preferably 10 to 20 parts by mass. When the amount of dihydric alcohol satisfies such a range, the cosmetic ink tends to have a viscosity within the desired range.

(C) Purified Water

A cosmetic ink according to the present disclosure includes (C) purified water. The (C) purified water also functions as a solvent of the cosmetic ink. After printing with the cosmetic ink on a printing medium, the (C) purified water is absorbed by or evaporates from the printing medium.

The (C) purified water is not particularly limited as long as it is ordinarily used for cosmetics, and may be water obtained as a result of purification by various methods such as distillation or ion-exchange; examples include hot spring water, deep ocean water, and water obtained by steam distillation of plants.

The amount of (C) purified water relative to 100 parts by mass of the cosmetic ink is preferably 10 parts by mass or more, more preferably 20 parts by mass or more.

(D) Acrylic-Based Resin (Binder)

A cosmetic ink according to the present disclosure includes (D) a binder. The (D) binder is a compound for binding the above-described (A) colorant and the like to a printing medium. In a cosmetic ink according to the present disclosure, the "binder" is preferably a particulate resin insoluble in the (B) higher alcohol and the (C) purified water. The cosmetic ink may include, as the (D) binder, one species alone or two or more species.

Examples of the (D) binder include particles formed of, for example, a (meth)acrylic-based resin such as an alkyl (meth)acrylate polymer, a styrene-(meth)acrylic copolymer, an alkyl (meth)acrylate-vinyl acetate copolymer, a (meth) acrylic acid-alkyl (meth)acrylate copolymer, or an alkyl (meth)acrylate dimethicone polymer. Incidentally, in this Description, (meth)acrylic means acrylic, methacrylic, or a mixture of acrylic and methacrylic.

Of these, the (D) binder is preferably particles formed of a (meth)acrylic-based resin (hereafter, also simply referred to as "acrylic-based particles"). When the (D) binder is constituted by acrylic-based particles, the (A) colorant tends to exhibit improved fixability, and the printed matter tends to have improved durability. More preferably, the (D) binder is formed of a (meth)acrylic-based resin free from skin irritation. Thus, the acrylic-based particles are preferably selected from, for example, the components listed in "List of Cosmetic Ingredient Label Names" based on Japan Pharmaceutical Affairs Law, the components in compliance with EU Cosmetics Directive (Cosmetics Directive 76/768/EEC), and the components described in International Cosmetic Ingredient Dictionary and Handbook (Jan. 1, 2002, 9th edition) published by U.S. CTFA (Cosmetic, Toiletry & Fragrance Association, U.S.), and may be particles of an acrylic-based resin used for, for example, publicly known cosmetics.

Specific examples of the (meth)acrylic-based resin constituting the acrylic-based particles include a homopolymer of a (meth)acrylic-based monomer, a copolymer of two or more (meth)acrylic-based monomer species, and a copolymer of a (meth)acrylic-based monomer and another monomer.

Examples of the (meth)acrylic-based monomer include acrylic acid, methyl acrylate, ethyl acrylate, acrylic acid amide, n-propyl acrylate, n-butyl acrylate, isobutyl acrylate, octyl acrylate, 2-ethylhexyl acrylate, N,N-dimethylaminoethyl acrylate, acrylonitrile, methacrylic acid, ethyl methacrylate, methacrylic acid amide, n-propyl methacrylate, n-butyl methacrylate, isobutyl methacrylate, 2-ethylhexyl methacrylate, octyl methacrylate, hydroxyethyl methacrylate, and N,N-dimethylaminoethyl methacrylate.

Examples of another monomer that can be copolymerized with the above-described (meth)acrylic-based monomer include styrene, vinyl acetate, a silicone macromer, a fluorinated monomer, and an alkoxysilane unsaturated monomer.

The (D) binder preferably has an average particle size of 30 nm to 150 nm. This average particle size is the median (D50) of the cumulative value of the particle size distribution measured by laser diffractometry. More preferably, the average particle size (D50) is 30 nm to 150 nm, and a value (D90) at 90% of the cumulative value of the particle size distribution is 250 nm or less. When the (D) binder has an average particle size satisfying such a range, the (A) colorant and the like are easily bound to a printing medium.

The amount of (D) binder included in 100 parts by mass of the cosmetic ink is preferably 0.1 parts by mass or more and 10 parts by mass or less, more preferably 2.5 to 10 parts by mass. The amount of (D) binder may be less than 0.1 parts by mass; however, when the amount is 0.1 parts by mass or more, the cosmetic ink tends not to undergo ink-repellency on a printing medium. On the other hand, when the amount of (D) binder is excessively large, the cosmetic ink may have an excessively high viscosity; however, when the amount is 10 parts by mass or less, the resultant viscosity is suitable for printing performed by various printing methods.

When the amount of (A) colorant in the cosmetic ink is set to 10 parts by mass, the amount of (D) binder is preferably 0.5 to 10 parts by mass, more preferably 1.5 to 5.7 parts by mass. When the amount of (D) binder relative to the amount of (A) colorant satisfies such a range, the (A) colorant exhibits higher fixability in the printed matter obtained using the cosmetic ink. However, when the amount of (D) binder is excessively large, as described above, the cosmetic ink tends to have an excessively high viscosity.

Incidentally, in the preparation of the cosmetic ink, the (D) binder ordinarily in a state of being dispersed in a dispersion medium (slurry or dispersion liquid) is mixed with the (A) colorant, the (B) higher alcohol, the (C) purified water, and the like. In this case, the dispersion medium is also preferably a solvent free from skin irritation, preferably the above-described higher alcohol or water.

Others

As described above, a cosmetic ink according to the present disclosure further includes (E) a film-forming agent and may optionally include various additives.

When the cosmetic ink includes the film-forming agent, it tends to have a higher film formability (such as drying properties). Incidentally, in this Description, "film-forming agent" is defined as a compound dispersible in water at room temperature; however, the film-forming agent does not encompass components corresponding to the above-described (D) binder. The cosmetic ink may include, as the film-forming agent, one species alone or two or more species.

The film-forming agent may be a compound that is dispersible in the (B) higher alcohol and/or the (C) purified water: for example, one or more compounds selected from the group consisting of acrylic-based polymers, polysaccharide-based polymers, sugar alcohol, sterols, esters, and corn starch modified. The cosmetic ink may include, as the film-forming agent, one species alone or two or more species. When the film-forming agent is a compound selected from the above-described group, the coating film formed of the cosmetic ink dries very rapidly.

The film-forming agent preferably has an HLB value of 8 or more, more preferably 8 to 19. When the film-forming agent has an HLB value of 8 or more, the film-forming agent tends to be uniformly dispersed or dissolved in the (B) higher alcohol, the (C) purified water, and the like. The HLB value is an index representing, in an oil-water system, a relative affinity ratio for the two liquids. In general, a substance having a large HLB value has a high affinity for water. Incidentally, in this Description, HLB values are values measured by the Griffin method.

The film-forming agent is also preferably a material free from skin irritation. Examples of the acrylic-based polymer include an alkyl acrylate copolymer, a 2-amino-2-methyl-1-propanol salt (hereafter, also referred to as "AMP") of an alkyl acrylate copolymer, a sodium salt (hereafter, also referred to as "Na") of an alkyl acrylate copolymer, an ammonium alkyl acrylate copolymer, an acrylic acid/alkyl acrylate copolymer, an alkyl acrylate/diacetone acrylamide copolymer, an AMP-alkyl acrylate/diacetone acrylamide copolymer, a 2-amino-2-methyl-1,3-propanediol salt (hereafter, also referred to as "AMPD") of an alkyl acrylate/diacetone acrylamide copolymer, a hydroxyethyl acrylate/methoxyethyl acrylate copolymer, a hydroxyethyl acrylate/butyl acrylate/methoxyethyl acrylate copolymer, an AMP-acrylates/C1-18 alkyl acrylate/C1-8 alkyl acrylamide copolymer, an alkyl acrylate/octyl acrylamide copolymer, an acrylates/t-butylacrylamide copolymer, an acrylates/ethylhexyl acrylate copolymer, an acrylates copolymer, an AMP-acrylates copolymer, a Na acrylates copolymer, an AMP-polyurethane-14/acrylates copolymer, a vinyl acetate/butyl maleate/isobornyl acrylate copolymer, a styrene/alkyl acrylate copolymer, a styrene/acrylates copolymer, a styrene/acrylic acid amide copolymer, polyurethane-1 (compound labelled with INCI name: POLYURETHANE-1), polyacrylate-22 (compound labelled with INCI name: POLYACRYLATE-22), triacontanyl polyvinylpyrrolidone (PVP), an (eicosane/vinylpyrrolidone) copolymer, and a (vinylpyrrolidone/hexadecene) copolymer.

Examples of the saccharide-based polymer include gum arabic, glucan, succinoglycan, carrageenan, gum karaya, gum traganth, guar gum, locust bean gum, galactomannan gum, xanthan gum, starch, carob gum, quince seeds (*Cydonia oblonga*), casein, dextrin, gelatin, sodium pectate, sodium alginate, methylcellulose, ethylcellulose, carboxymethylcellulose, hydroxyethylcellulose, hydroxypropylcellulose, crystalline cellulose, O-[2-hydroxy-3-(trimethylammonio)propyl]hydroxyethylcellulose chloride, O-[2-hydroxy-3-(trimethylammonio)propyl]guar gum chloride, O-[2-hydroxy-3-(trimethylammonio)propyl]locust bean gum chloride, hydroxypropyltrimonium starch chloride, glyceryl glucosid, glycosyl trehalose, Tremella Fuciformis polysaccharide, and dextrin isostearate.

Examples of the sugar alcohol include sorbitol, maltitol, and glucose. The sterols are compounds at least having a sterol skeleton; examples include phytosterols such as campesterol, campestanol, brassicasterol, 22-dehydrocampesterol, stigmasterol, stigmastanol, 22-dihydrospinasterol, 22-dehydrostigmastanol, 7-dehydrostigmasterol, sitosterol, tirucallol, euphol, fucosterol, isofucosterol, codisterol, clionasterol, poriferasterol, clerosterol, 22-dehydroclerosterol, fungisterol, chondrillasterol, avenasterol, vernosterol, and pollinastanol; zoosterols such as cholesterol, dihydrocholesterol, cholestanol, coprostanol, epicoprosterol, epicoprostanol, 22-dehydrocholesterol, desmosterol, 24-methylenecholesterol, lanosterol, 24,25-dihydrolanosterol, norlanosterol, spinasterol, dihydroagnosterol, agnosterol, lophenol, and lathosterol; mycosterols such as dehydroergosterol, 22,23-dihydroergosterol, episterol, azacosterol, and fecosterol; and hydrogenated products of the foregoing.

Examples of the esters include dipentaerythritol fatty acid esters such as dipentaerythrityl hexa(hydroxystearate/stearate/rosinate), dipentaerythrityl (hydroxystearate/stearate/rosinate), dipentaerythrityl hexahydroxystearate, dipentaerythrityl tetra(hydroxystearate/isostearate), and dipentaerythrityl (hydroxystearate/isostearate); hydrogenated castor oil fatty acid esters such as hydrogenated castor oil stearate, hydrogenated castor oil isostearate, and hydrogenated castor oil hydroxystearate; cholesterol fatty acid esters such as cholesteryl hydroxystearate; phytosterol fatty acid esters such as phytosteryl oleate and phytosteryl macadamiate; hydrogenated vegetable oils such as hydrogenated coconut oil and hydrogenated palm oil; (phytosteryl/isostearyl/cetyl/stearyl/behenyl) dimer dilinoleate; sucrose pentahydroxystearate; and di(octyldodecyl/phytosteryl/behenyl) lauroyl glutamate.

The corn starch modified may be a compound obtained by modifying corn starch with any compound as long as an object and advantages of the present disclosure are not hindered: for example, hydroxypropyl-modified starch obtained by causing 3-(dodecenyl)dihydro 2,5-furandione to react with corn starch.

Among those described above, from the viewpoint of providing cosmetic inks having improved drying properties, preferred are the acrylates copolymer, the acrylates (ethylhexyl acrylate) copolymer, the AMP polyurethane-14/acrylates copolymer, the ammonium alkyl acrylate copolymer, bis(behenyl/isostearyl/phytosteryl) dimer dilinoleyl dimer dilinoleate, triglyceryl hydrogenated rosinate, the xanthan gum crosspolymer, hydroxyethylcellulose, Tremella Fuciformis polysaccharide, corn starch modified, and dextrin isostearate; more preferred are the acrylates copolymer, the acrylates (ethylhexyl acrylate) copolymer, the AMP polyurethane-14/acrylates copolymer, the ammonium alkyl acrylate copolymer, bis(behenyl/isostearyl/phytosteryl) dimer dilinoleyl dimer dilinoleate, triglyceryl hydrogenated rosinate, the xanthan gum crosspolymer, hydroxyethylcellulose, and Tremella Fuciformis polysaccharide.

Incidentally, the film-forming agent content relative to 100 parts by mass of the cosmetic ink is preferably 20 parts by mass or less, more preferably 0.3 to 5 parts by mass. When the film-forming agent content is 0.3 parts by mass or more, as described above, the cosmetic ink has improved drying properties. On the other hand, when the film-forming agent content is excessively high, the cosmetic ink may have an excessively high viscosity; however, when the content is 20 parts by mass or less, the resultant cosmetic ink has a viscosity suitable for printing performed by various printing methods.

In the preparation of the cosmetic ink, ordinarily, the film-forming agent being dissolved in a solvent so as to be in the state of a solution is mixed with the (A) colorant, the (B) higher alcohol, the (C) purified water, and the like. The solvent used in this case is also preferably a solvent free from skin irritation, preferably the above-described higher alcohol or water.

The cosmetic ink may further include various additives as long as an object and advantages of the present disclosure are not hindered. The various additives are preferably compounds free from skin irritation. Examples of the various additives include a surfactant, a pH adjusting agent, a thickening agent, an ultraviolet absorbent, an ultraviolet scattering agent, an antimicrobial agent, a deoxidation agent, an antioxidant, a preservative, an anti-fading agent, a foam breaker, a perfume, and a solvent other than the (B) higher alcohol and the (C) purified water.

The cosmetic ink may further include, for example, a water-soluble polymer (polymer not belonging to the above-described film-forming agent) for binding to a printing medium as long as an object and advantages of the present disclosure are not hindered.

Method for Preparing Cosmetic Ink

The above-described cosmetic ink is obtained by, for example, mixing, using a dispersion apparatus, the (A) colorant, the (B) higher alcohol, the (C) purified water, a slurry or dispersion liquid including the (D) acrylic-based resin, the (E) film-forming agent, and optionally another component. Such components can be mixed using, for example, a publicly known dispersion apparatus such as a ball mill, a sand mill, a roll mill, a homomixer, or an attritor.

1-2. Physical Properties of Cosmetic Ink

The above-described cosmetic ink has a viscosity at 25° C. of, measured using a cone-plate viscometer, at a rate of 1000 (1/s), preferably 50 mPa·s or less, more preferably 1 to 20 mPa·s, still more preferably 3.5 to 8 mPa·s. When the cosmetic ink has a viscosity satisfying such a range, the cosmetic ink is easily used for printing using various printing apparatuses. In particular, when the viscosity satisfies such a range, stable ejection from ink jet apparatuses tends to be achieved.

The cosmetic ink preferably has a pH of 6 to 10, more preferably 7.5 to 9.5. When the cosmetic ink has a pH satisfying such a range, the cosmetic ink does not, for example, corrode members of various printing apparatuses; in addition, even in the case of storage of the cosmetic ink for a long period of time, the (A) colorant tends not to, for example, aggregate, so that coating films of the desired color tend to be obtained.

The cosmetic ink preferably has a surface tension at 25° C. of 50 mN/m or less, more preferably 32 mN/m to 46 mN/m. When the surface tension is 50 mN/m or less, upon application of the cosmetic ink from various printing apparatuses to various printing media, the cosmetic ink has improved wettability and films having a uniform thickness can be formed. Incidentally, surface tension can be determined by various measurement methods; however, the above-described values are values measured by the pendant drop method employed in commonly used apparatuses.

The particles included in the cosmetic ink have an average particle size, specifically a median (D50) of the cumulative value of the particle size distribution measured by laser diffractometry, the median (D50) being preferably 125 nm or more and 2 μm or less; more preferably the average particle size (D50) is 125 nm or more and 1000 nm or less; still more preferably, the average particle size (D50) is 125 nm or more and 1000 nm or less, and a value (D90) at 90% of the cumulative value of the particle size distribution is 3000 nm or less. When the particles included in the cosmetic ink have an average particle size satisfying such a range, stable ejection from various printing apparatuses, particularly from ink jet apparatuses, can be achieved. When the value of D50 or D90 satisfies such a range, the cosmetic ink can be stably ejected from ink jet apparatuses, for example.

The cosmetic ink is preferably negative in terms of skin irritation, specifically, has high safety for living bodies. Such a cosmetic ink prepared to be negative in terms of skin irritation can also be used in applications in contact with the skin, for example. In the present disclosure, "negative in terms of skin irritation" means that, in the case of performing, as an alternative for the skin irritation test, a test using a three-dimensional skin model, the cell viability is more than 50%. The alternative for the skin irritation test employs a 5% sodium dodecyl sulfate (SDS) solution as an irritation-positive control, and a phosphate buffered saline (PBS) as a negative control. After exposure of the three-dimensional skin model to the ink for 18 hours, MTT assay is performed to evaluate cell viability.

An example of a method for providing a cosmetic ink that is negative in terms of skin irritation is to select all the components included in the cosmetic ink from, for example, the components listed in "List of Cosmetic Ingredient Label Names" based on Japan Pharmaceutical Affairs Law, the components in compliance with EU Cosmetics Directive (Cosmetics Directive 76/768/EEC), and the components described in International Cosmetic Ingredient Dictionary and Handbook (Jan. 1, 2002, 9th edition) published by U.S. CTFA (Cosmetic, Toiletry & Fragrance Association, U.S.).

1-3. Ink Cartridge

The above-described cosmetic ink can be charged into, for example, a cartridge and stored. The species and structure of the cartridge are not particularly limited, and are appropriately selected in accordance with the printing apparatus for printing using the cosmetic ink. Such an ink cartridge is, for example, a cartridge including an ink container for containing the cosmetic ink, and an ink supply port for supplying the ink to the recording head of the printing apparatus.

2. Method for Producing Cosmetic Sheet 2-1. Method for Producing Cosmetic Sheet Using Above-Described Cosmetic Ink A production method including a step of performing printing using the above-described cosmetic ink on a printing medium, and a step of drying the cosmetic ink applied to the printing medium, enables production of a cosmetic sheet.

The process of performing printing using the cosmetic ink on a printing medium is not particularly limited, and may be a publicly known process. Examples of such a printing process include an ink jet printing process, a screen printing process, offset printing, and gravure printing. Of these, the ink jet process is preferred from the viewpoint of facilitating on-demand printing performed in accordance with, for example, the conditions or color of the skin of the user of the cosmetic sheet, and enabling multilayer printing of applying the cosmetic ink a plurality of times. Hereinafter, the method of producing a cosmetic sheet will be described with reference to an example case of printing using the cosmetic ink by an ink jet process; however, the present disclosure is not limited to this method.

In the case of applying the cosmetic ink to a printing medium by the ink jet process, the ink jet apparatus is not particularly limited, and may be any apparatus of the publicly known piezoelectric mode, thermal mode, or electrostatic mode. Of these, an ink jet apparatus of a piezoelectric device mode is preferred from the viewpoint of unnecessity of heating performed in the thermal ink jet mode.

The cosmetic ink may be applied to, a printing medium, a single time alone, or two or more times. Incidentally, in the case of applying the cosmetic ink to a printing medium a plurality of times, the cosmetic ink may be dried after each application, or may be dried after a plurality of applications. A cosmetic ink according to the present disclosure has relatively good drying properties. Thus, even in the case of performing the step of drying after a plurality of applications, drying can be achieved in a short period of time.

Incidentally, since the coating film has the above-described spectral reflectances, regardless of whether a cosmetic ink according to the present disclosure is applied in a small amount or a large amount, the coating film can be made to have a color close to the color of the human skin. Thus, the coverage rate (the area of adhesion of the cosmetic ink relative to the area of the region to which the cosmetic ink is applied) can be freely adjusted in accordance with the usage.

The process of drying the cosmetic ink applied to a printing medium is not particularly limited as long as it is a process that enables removal of the (B) higher alcohol and the (C) purified water from the cosmetic ink. Examples of the process include a process of performing drying at atmospheric pressure at room temperature, and a process of heating at a predetermined temperature and/or reducing the pressure to achieve drying. In the case of performing heating, heating at, for example, 25 to 50° C. is preferred. In such a range, without causing deterioration of the printing medium or the solid content of the cosmetic ink, drying can be efficiently achieved. On the other hand, in the case of reducing the pressure, a reduction to −0.1 to 0 MPa is preferred. Such a reduction in the pressure to this range achieves efficient drying of the ink.

The printing medium to which the above-described cosmetic ink is applied is not particularly limited as long as an object and advantages of the present disclosure are not hindered. Articles similar to the substrates of publicly known cosmetic sheets may be employed as the printing medium. Examples of the printing medium include plain paper, dedicated recording paper, plastic, and cloth. The printing medium may be constituted by a single layer alone, or by a stack of two or more layers. Of these, in particular, preferred are various sheets that are directly or indirectly affixed or adhered to the skin, and that are composed of biocompatible materials.

Examples of the biocompatible materials include polyesters represented by polyglycolic acid, polylactic acid, polycaprolactone, polyethylene succinate, polyethylene terephthalate, and copolymers of the foregoing; polyethers represented by polyethylene glycol and polypropylene glycol; polyamides represented by nylon, polyglutamic acid, polyaspartic acid, and salts of the foregoing; polysaccharides represented by pullulan, cellulose, starch, chitin, chitosan, alginic acid, hyaluronic acid, corn starch, and salts of the foregoing; silicones represented by acrylic silicone and trimethylsiloxysilicic acid; acrylic acids such as alkyl acrylate, acrylic acid silicone, acrylic acid amide, and copolymers of the foregoing; polyvinyl alcohol; polyurethane; polycarbonate; poly acid anhydride; polyethylene; polypropylene; porous layer coating sheets and nanofiber sheets. Examples of the sheets composed of biocompatible materials include sheets for fastening medical materials, sheets for sports taping, sheets for skin decoration, cosmetic sheets, and surgical anti-adhesion materials.

The thickness of the printing medium is not particularly limited, and is appropriately selected in accordance with, for example, the species or usage of the printing medium, for example, 10 µm or less. When the printing medium has a small thickness, the printing medium is less likely to absorb the solvent (such as the (B) higher alcohol and the (C) purified water), so that the ink is less likely to dry. By contrast, a cosmetic ink according to the present disclosure has improved drying properties; for example, even on a printing medium having a thickness of 3000 nm or less, printing can be achieved; for example, even on a thin film of 10 nm or more and 1000 nm or less, printing can be achieved.

Incidentally, in the case of forming an image on a printing medium constituted by such a thin film, printing may be performed on a multilayered body of a stack of the printing medium and a support supporting the printing medium, and, after the printing, the thin film may be released from the support. The support is not particularly limited, but may be composed of, for example, a material having high water absorbency. When the support has water absorbency, the support can be used to rapidly absorb the (B) higher alcohol and the (C) purified water, so that the solid content alone of the cosmetic ink can be made to firmly adhere to the surface of the printing medium. Thus, the resultant image is less likely to undergo, for example, bleeding, so that a high-definition image can be formed. Examples of the support having high water absorbency include substrates composed of paper, cloth, nonwoven fabric, woven fabric, a porous layer coating sheet, a nanofiber sheet, a water-absorbent polymer, or a water-soluble polymer.

2-2. Method for Producing Cosmetic Sheet Using Cosmetic Inks of Plurality of Colors Alternatively, the cosmetic sheet can also be produced by, a production method including a coating film formation step of applying, to positions displaced from each other, droplets of inks of three or more colors selected from the group consisting of white ink, red ink, yellow ink, blue ink, and black ink, to form a coating film, and a drying step of drying the cosmetic inks applied to the printing medium. Incidentally, the drying step may be performed as with the drying step of the above-described method for producing a cosmetic sheet using the cosmetic ink. Thus, hereafter, the coating film formation step alone will be described.

In the coating film formation step according to this embodiment, the inks of different colors are applied to positions displaced from each other, to thereby form a coating film having predetermined spectral reflectances. More specifically, a coating film is formed such that the spectral reflectance curve in wavelengths of 400 nm to 700 nm has a first inflection point in a wavelength region of 550 nm or more and 610 nm or less, and a second inflection point in a wavelength region of less than 550 nm. In addition, the spectral reflectance at the first inflection point is higher than the spectral reflectance at the second inflection point; and the spectral reflectances in a wavelength region of 610 nm or more are equal to or higher than the spectral reflectance at the first inflection point. When the coating film has such spectral reflectances, as described above, the color difference from the color of the human skin is small, and the cosmetic sheet affixed is less noticeable. Incidentally, the spectral reflectances in a wavelength region of 590 nm to 700 nm of the coating film are preferably similar to the spectral reflectances in a wavelength region of 590 nm to 700 nm of the coating film of the above-described cosmetic ink; in addition, the lightness of the coating film is also preferably similar to the lightness of the coating film of the above-described cosmetic ink.

In the coating film formation step according to this embodiment, ink droplets of three or more colors selected from the group consisting of white ink, red ink, yellow ink, blue ink, and black ink are applied, to form a coating film having the above-described spectral reflectances. In this case, combination of at least white ink, red ink, and yellow ink tends to achieve the above-described spectral reflectances. In addition, further combination with blue ink and black ink enables adjustments, to desired ranges, the spectral reflectances in wavelengths of 590 nm to 700 nm of the coating film and the lightness of the coating film. Incidentally, the order of applying the inks of different colors is not particularly limited; any color ink may be first applied, to obtain a coating film having similar spectral reflectances.

In the coating film formation step, the amounts of inks applied are not particularly limited as long as the above-described spectral reflectances are achieved. For example, the proportions of, in the inks of different colors, the white-based colorant, the red-based colorant, the yellow-based colorant, the blue-based colorant, and the black-based colorant may be set similar to the proportions of, in the above-described cosmetic ink, the white-based colorant, the red-based colorant, the yellow-based colorant, the blue-based colorant, and the black-based colorant.

The compositions of the white ink, the red ink, the yellow ink, the blue ink, and the black ink applied in this embodiment are not particularly limited; however, each ink preferably includes the (A) colorant, the (B) higher alcohol having 3 or more carbon atoms, the (C) purified water, the (D) acrylic-based resin, and the (E) film-forming agent. Thus, the ink preferably has the same composition as in the above-described cosmetic ink except that it includes, as the (A) colorant, a single-color colorant alone, from the viewpoint of, for example, drying properties and low skin irritation of the ink.

In ordinary printing apparatuses, ink droplets of a plurality of colors are dropped to the same position of a printing medium so as to overlap, to thereby reproduce a desired color. By contrast, in the coating film formation step according to this embodiment, inks of different colors are dropped to positions displaced from each other, to form a coating film. The ink droplets caused to adhere during production of the cosmetic sheet ordinarily have such small diameters that each dot cannot be visually recognized. Thus, even in the case of performing printing such that inks of different colors are applied to positions displaced from each other, these colors are observed as a mixed color by the naked eye, and the coating film can be recognized as having the above-described spectral reflectances.

In this way, the coating film is formed to form a cosmetic sheet, to thereby achieve a reduction in the area of regions to which ink-derived pigments do not adhere. Thus, in the case of affixing the cosmetic sheet to, for example, a discolored area of the skin such as a blotch, the discolored area markedly becomes less noticeable. In particular, when the white-based colorant derived from the white ink adheres to the surface of the printing medium, the white-based colorant tends to exert its light scattering effect, to make the discolored area even less noticeable.

In the coating film formation step, the inks of different colors may be applied to positions that are displaced from each other such that ink droplets of different colors do not overlap; alternatively, the inks may be applied to positions that are displaced to a degree from each other such that ink droplets of different colors partially overlap. The inks of different colors may be applied so as to be regularly displaced from each other to form a coating film. However, more preferably, the inks of different colors are applied to random positions to make ink droplets of different colors displaced from each other, from the viewpoint that, for example, the cosmetic sheet affixed makes the discolored area of the skin less noticeable.

In the coating film formation step according to this embodiment, the process of applying the inks of different colors is not particularly limited, and may be any of, for example, an ink jet printing process, a screen printing process, offset printing, and gravure printing. However, of these, the ink jet process is preferred from the viewpoint of facilitating random application of the inks of different colors.

In the case of forming a coating film by the ink jet process, the ink tanks of an ink jet apparatus are individually filled with a white ink, a red ink, a yellow ink, a blue ink, and a black ink. Subsequently, the ink jet apparatus is used to perform printing using the first color; subsequently, the nozzles or the printing medium is moved in a predetermined direction or rotated and printing using the second color is performed. Similarly, during printing using the third color etc., the nozzles or the printing medium is moved in a predetermined direction or rotated. In this way, ink droplets of different colors can be made to land to positions appropriately displaced from each other.

Incidentally, the printing medium to which the inks are applied may be similar to the printing medium used in the above-described method for producing a cosmetic sheet using a cosmetic ink.

EXAMPLES

Hereinafter, the present disclosure will be described with reference to Examples. Examples do not limit the scope of the present disclosure.

1. Cosmetic Inks a
1-1. Materials
The following are materials used for Examples and Comparative Examples. Incidentally, the average particle sizes of the particles are each the median (D50) of the cumulative value of a particle size distribution measured by laser diffractometry.

(A) Colorant
Red-based colorant: inorganic red-based pigment (average particle size: 150 nm)
Yellow-based colorant: inorganic yellow-based pigment (average particle size: 150 nm)
Blue-based colorant: inorganic blue-based pigment (average particle size: 150 nm)
Black-based colorant: inorganic black-based pigment (average particle size: 150 nm)
White-based colorant: inorganic white-based pigment (average particle size: 120 nm)
(B) Higher Alcohol
Glycerol
1,3-Propanediol
(C) Purified Water
(D) Binder
Acrylic-based polymer particles (average particle size: 50 nm)

1-2. Preparation of Cosmetic Inks

The materials were mixed in component ratios described in Table 1 and Table 2 below to prepare cosmetic inks. Incidentally, Table 1 also describes the mass ratios of colorants of different colors included in the (A) colorant.

1-3. Evaluation 1

Physical properties of the cosmetic inks were evaluated in the following manner. The results are described in Table 1 and Table 2. FIG. 1 and FIG. 2 illustrate the spectral reflectance curves of the cosmetic inks, the spectral reflectance curve of the skin model, and the spectral reflectance curves of the human skin (cheek and the medial region of arm).

Methods of Measuring Viscosity, pH, and Surface Tension of Cosmetic Inks

The viscosity of the cosmetic inks was measured using a cone-plate viscometer at 25° C. and at a shear rate of 1000 (1/s). The pH of the cosmetic inks was measured using a pH meter (LAQUAtwin, manufactured by HORIBA, Ltd.). The surface tension of the cosmetic inks was measured using a contact angle meter (DropMaster DM-501, manufactured by Kyowa Interface Science Co., Ltd.).

Methods of Measuring Spectral Reflectance and Lightness ($L^*$ Value)

The spectral reflectance and lightness ($L^*$ value) are values obtained by measuring a coating film formed from a cosmetic ink, using, in a wavelength region of 400 nm to 700 nm, a spectrophotometer (such as CM-700d manufactured by KONICA MINOLTA JAPAN, INC.) with a main light source of D50 and a measurement mode of SCE.

TABLE 1

| | | Example | | | | | Comparative Example | | | |
|---|---|---|---|---|---|---|---|---|---|---|
| | | A-1 | A-2 | A-3 | A-4 | A-5 | A-6 | A-7 | A-8 | A-9 |
| (A) Colorant | Total amount of pigment (mass %) | 10 to 15 | 10 to 15 | 10 to 15 | 10 to 15 | 10 to 15 | 10 to 15 | 10 to 15 | 10 to 15 | 10 to 15 |
| | Red-based colorant (mass ratio) | | | | 0.1 to 20 | | | | | |
| | Yellow-based colorant (mass ratio) | | | | 0.1 to 20 | | | | | |
| | Blue-based colorant (mass ratio) | 0 | 0.25 | 0.5 | 0.75 | 1.0 | 2.0 | 3.0 | 5.0 | 10.0 |
| | Black-based colorant (mass ratio) | | | | 0 | | | | | |
| | White-based colorant (mass ratio) | | | | 60 to 99.8 | | | | | |
| (B) Higher alcohol | Glycerol (mass %)/ 1,3-Propanediol (mass %) | | | | 10/10 | | | | | |
| (C) Purified water (mass %) | | | | | 62.5 to 67.5 | | | | | |
| (D) Binder | Acrylic-based polymer particles (mass %) | | | | 2.5 | | | | | |
| Spectral reflectance curve | Presence or absence of first inflection point and second inflection point | Present | Present | Present | Present | Present | Present | Present | Present | Present |
| | Spectral reflectances in wavelengths of more than 580 nm ≥ spectral reflectance at wavelength of 580 nm | Satisfied | Satisfied | Satisfied | Satisfied | Satisfied | Not satisfied | Not satisfied | Not satisfied | Not satisfied |
| Lightness ($L^*$ value) | | 71.94 | 72.79 | 71.93 | 70.86 | 65.91 | 60.32 | 65.63 | 60.59 | 50.55 |
| Viscosity (mPa·s) | | 5.5 | 5.5 | 5.5 | 5.5 | 5.5 | 5.5 | 5.5 | 5.5 | 5.5 |
| pH | | 8.0 | 8.0 | 8.0 | 8.0 | 8.0 | 8.0 | 8.0 | 8.0 | 8.0 |
| Surface tension (mN/m) | | 34 | 34 | 34 | 34 | 34 | 34 | 34 | 34 | 34 |

TABLE 2

| | | Example | | | | | | | | | Comparative Example |
|---|---|---|---|---|---|---|---|---|---|---|---|
| | | A-1 | A-10 | A-11 | A-12 | A-13 | A-14 | A-15 | A-16 | A-17 | A-18 | A-19 |
| (A) Colorant | Total amount of pigment (mass %) | 10 to 15 | 10 to 15 | 10 to 15 | 10 to 15 | 10 to 15 | 10 to 15 | 10 to 15 | 10 to 15 | 10 to 15 | 10 to 15 | 10 to 15 |
| | Red-based colorant (mass ratio) | | | | | | 0.1 to 20 | | | | | |
| | Yellow-based colorant (mass ratio) | | | | | | 0.1 to 20 | | | | | |
| | Blue-based colorant (mass ratio) | | | | | | 0 | | | | | |

TABLE 2-continued

|  |  | Example |  |  |  |  |  |  |  |  |  | Comparative Example |
|---|---|---|---|---|---|---|---|---|---|---|---|---|
|  |  | A-1 | A-10 | A-11 | A-12 | A-13 | A-14 | A-15 | A-16 | A-17 | A-18 | A-19 |
|  | Black-based colorant (mass ratio) | 0 | 0.25 | 0.3 | 0.5 | 0.6 | 0.75 | 1.0 | 2.0 | 3.0 | 5.0 | 10.0 |
|  | White-based colorant (mass ratio) |  |  |  |  | 60 to 99.8 |  |  |  |  |  |  |
| (B) Higher alcohol | Glycerol (mass %)/ 1,3-Propanediol (mass %) |  |  |  |  | 10/10 |  |  |  |  |  |  |
| (C) Purified water (mass %) |  |  |  |  |  | 62.5 to 67.5 |  |  |  |  |  |  |
| (D) Binder | Acrylic-based polymer particles (mass %) |  |  |  |  | 2.5 |  |  |  |  |  |  |
| Spectral reflectance curve | Presence or absence of first inflection point and second inflection point | Present | Present | Present | Present | Present | Present | Present | Present | Present | Present | Absent |
|  | Spectral reflectances in wavelengths of more than 580 nm ≥ spectral reflectance at wavelength of 580 nm | Satisfied | Satisfied | Satisfied | Satisfied | Satisfied | Satisfied | Satisfied | Satisfied | Satisfied | Satisfied | Satisfied |
| Lightness (L* value) |  | 71.94 | 72.42 | 68.34 | 69.88 | 67.37 | 67.00 | 67.05 | 59.53 | 56.40 | 54.08 | 43.66 |
| Viscosity (mPa · s) |  | 5.5 | 5.5 | 5.5 | 5.5 | 5.5 | 5.5 | 5.5 | 5.5 | 5.5 | 5.5 | 5.5 |
| pH |  | 8.0 | 8.0 | 8.0 | 8.0 | 8.0 | 8.0 | 8.0 | 8.0 | 8.0 | 8.0 | 8.0 |
| Surface tension (mN/m) |  | 34 | 34 | 34 | 34 | 34 | 34 | 34 | 34 | 34 | 34 | 34 |

As illustrated in FIG. 1 and FIG. 2, in each of Cosmetic inks A-1 to A-5 and A-11 to 15, the coating film had a spectral reflectance curve having, in the wavelength region of 550 nm or more and 610 nm or less, a first inflection point, and, in the wavelength region of less than 550 nm, a second inflection point. In each of these cosmetic inks, the spectral reflectance at the first inflection point was higher than the spectral reflectance at the second inflection point. In addition, in each of these cosmetic inks, spectral reflectances throughout the wavelength region of more than 580 nm were equal to or higher than the spectral reflectance at a wavelength of 580 nm. These coating films having such spectral reflectances and obtained from the cosmetic inks were visually compared with the skin model in terms of color, and the color differences were found to be small.

By contrast, the color differences from the skin model were found to be large in Cosmetic ink A-19 not having one or both of the first inflection point and the second inflection point, and in Cosmetic inks A-6 to A-9 in which spectral reflectances in the wavelength region of more than 580 nm were partially lower than the spectral reflectance at a wavelength of 580 nm.

1-4. Evaluation 2

Cosmetic inks A-1, A-3, A-12, and Cosmetic ink A-20 prepared by mixing A-2 and A-10 in 1:1 were charged into the ink tanks of an ink jet apparatus including an LB3 ink jet head manufactured by Panasonic Precision Device Co., Ltd. Incidentally, regarding Cosmetic ink A-20, the spectral reflectance curve of a coating film was examined in the above-described manner: as a result, the spectral reflectance curve had, in the wavelength region of 550 nm or more and 610 nm or less, a first inflection point, and, in the wavelength region of less than 550 nm, a second inflection point. In each of these cosmetic inks, the spectral reflectance at the first inflection point was higher than the spectral reflectance at the second inflection point. In addition, in each of these cosmetic inks, spectral reflectances throughout the wavelength region of more than 580 nm were equal to or higher than the spectral reflectance at a wavelength of 580 nm.

On the other hand, a printing medium was prepared by bonding a polylactic acid sheet having a thickness of 200 nm to a support composed of filter paper. The above-described cosmetic inks were individually applied onto the polylactic acid sheet at coverage rates described in Table 3. The printed patterns were 15 mm×15 mm square solid patterns. The coverage rate is a ratio of the area of adhesion of a cosmetic ink to the area for printing (15 mm×15 mm). The sheet after printing was dried in an environment at 50° C.

The obtained coating films were measured using a spectrophotometer (such as CM-700d manufactured by KONICA MINOLTA JAPAN, INC.) with a main light source of D50 and a measurement mode of SCE, in terms of L* value, a* value, and b* value in the L*a*b* color system. On the other hand, a skin model (BIOSKIN (manufactured by Beaulax Co., Ltd., Product number: BIO)) was also similarly measured in terms of L* value, a* value, and b* value in the L*a*b* color system. The color difference ΔE*ab between such a coating film and the skin model was calculated. The values are described in Table 3.

The color difference ΔE*ab was evaluated in accordance with the following grading system. Incidentally, Grades C or better correspond to the practically usable level.

AAA: color difference ΔE*ab is 0.4 or more and less than 0.8
AA: color difference ΔE*ab is 0.8 or more and less than 1.6
A: color difference ΔE*ab is 1.6 or more and less than 3.2
B: color difference ΔE*ab is 3.2 or more and less than 6.5
C: color difference ΔE*ab is 6.5 or more and less than 13.0
D: color difference ΔE*ab is 13.0 or more and less than 25.0

In addition, samples having small color differences ΔE*ab were also evaluated by visual inspection. In the visual inspection, evaluation was performed in accordance with the following grading system.

Excellent: the color is sensorily perceived to be completely the same as that of the skin model Good: the color is sensorily perceived to be the same as that of the skin model; however, gazing reveals that the color is very similar to but is different from that of the skin model colorants were adjusted such that the cosmetic inks applied would provide substantially uniform color densities.

2-3. Evaluation

TABLE 3

| | Cosmetic ink | Coverage rate [%] | Measured values | | | Color difference from skin model | | | | Evaluation | |
|---|---|---|---|---|---|---|---|---|---|---|---|
| | | | L* (D50) | a* (D50) | b* (D50) | ΔL* (D50) | Δa* (D50) | Δb* (D50) | ΔE*ab | Color difference evaluation | Visual inspection evaluation |
| Skin color (skin model) | — | — | 66.29 | 12.68 | 19.24 | — | — | — | — | — | — |
| White/Red/Yellow | A-1 | 20 | 67.9 | 12.28 | 18.55 | −0.75 | 0.48 | 1.67 | 1.892564 | A | |
| | | 40 | 67.03 | 13.52 | 22.54 | −1.67 | 1.69 | 5.44 | 5.936211 | B | |
| | | 60 | 66.28 | 14.59 | 25.49 | −2.74 | 2.83 | 8.57 | 9.431935 | C | |
| | | 80 | 65.55 | 15.61 | 27.81 | −3.52 | 3.87 | 10.88 | 12.07235 | C | |
| | | 100 | 64.66 | 16.68 | 30.14 | −4.31 | 4.87 | 13.08 | 14.60751 | D | |
| White/Red/Yellow/Blue | A-3 | 20 | 67.63 | 12.19 | 18.04 | −0.79 | 0.3 | 0.71 | 1.103721 | AA | Good |
| | | 40 | 66.82 | 13.08 | 21.3 | −2.02 | 1.3 | 4.21 | 4.847113 | B | |
| | | 60 | 66.04 | 13.99 | 24.14 | −2.88 | 2.2 | 7.01 | 7.891419 | C | |
| | | 80 | 64.99 | 14.77 | 26.4 | −3.76 | 2.94 | 9.21 | 10.3733 | C | |
| | | 100 | 64.42 | 15.56 | 28.44 | −4.5 | 3.74 | 11.16 | 12.60092 | C | |
| White/Red/Yellow/Black | A-12 | 20 | 67.87 | 11.84 | 17.05 | −0.86 | 0.06 | 0.08 | 0.865794 | AA | Good |
| | | 40 | 66.4 | 12.93 | 20.76 | −2.48 | 1.16 | 3.7 | 4.602825 | B | |
| | | 60 | 65.18 | 13.78 | 23.21 | −3.76 | 2 | 6.07 | 7.415019 | C | |
| | | 80 | 63.91 | 14.6 | 25.32 | −4.89 | 2.75 | 8.03 | 9.795688 | C | |
| | | 100 | 62.81 | 15.35 | 27.22 | −6 | 3.53 | 9.97 | 12.15984 | C | |
| White/Red/Yellow/Blue/Black | A-20 | 20 | 67.99 | 11.74 | 16.49 | −0.53 | −0.09 | −0.51 | 0.741013 | AAA | Excellent |
| | | 40 | 67.05 | 12.99 | 20.11 | −1.86 | 1.17 | 2.93 | 3.662431 | B | |
| | | 60 | 66.04 | 13.71 | 22.55 | −3.02 | 1.92 | 5.37 | 6.453193 | B | |
| | | 80 | 65.04 | 14.49 | 24.6 | −3.95 | 2.7 | 7.44 | 8.845683 | C | |
| | | 100 | 63.97 | 15.31 | 26.71 | −4.84 | 3.44 | 9.38 | 11.10151 | C | |

As described in Table 3 above, the cosmetic inks having the above-described spectral reflectances provided, in the cases of coverage rates of 80% or less, coating films having a color similar to that of the skin model. In particular, when the blue-based colorant and the black-based colorant were included, even in the case of a coverage rate of 100%, a coating film having a color similar to that of the skin model was provided. The coating films at a coverage rate of 20% and evaluated as very good were visually inspected and also evaluated as good.

2. Cosmetic Sheets 2-1. Materials

The following are materials used for Example and Comparative Example.

(A) Colorant

Red-based colorant: inorganic red-based pigment (average particle size: 150 nm)

Yellow-based colorant: inorganic yellow-based pigment (average particle size: 150 nm)

Blue-based colorant: inorganic blue-based pigment (average particle size: 150 nm)

Black-based colorant: inorganic black-based pigment (average particle size: 150 nm)

White-based colorant: inorganic white-based pigment (average particle size: 120 nm)

(B) Higher Alcohol

Glycerol 1,3-Propanediol (C) Purified Water (D) Binder

Acrylic-based polymer particles (average particle size: 50 nm)

2-2. Preparation of Cosmetic Inks

Cosmetic inks of white, red, yellow, blue, and black were prepared as with the cosmetic ink of Example 1 except that the inks each included a single colorant. The amounts of colorants were adjusted such that the cosmetic inks applied would provide substantially uniform color densities.

The white ink, the red ink, the yellow ink, the blue ink, and the black ink were charged into the ink tanks of an ink jet apparatus including an LB3 ink jet head manufactured by Panasonic Precision Device Co., Ltd. On the other hand, a printing medium was prepared by bonding a polylactic acid sheet having a thickness of 200 nm to a support composed of filter paper. Subsequently, the cosmetic inks were applied onto the polylactic acid sheet to form a circular pattern having a radius of 30 mm (solid pattern). At this time, every time after application of one of the colors, the polylactic acid sheet was rotated by an appropriate angle such that ink droplets of different colors would not overlap at all during the printing. In addition, at this time, the amounts of inks applied were adjusted such that the amounts of colorants included in the inks were substantially the same as the pigment ratios of the cosmetic ink of Example 1 above. The sheet after the printing was dried in an environment at 50° C., to obtain Cosmetic sheet B-1 (Example).

On the other hand, in the same manner as above, a circular pattern having a radius of 30 mm (solid pattern) was formed with the same amounts of inks applied (volume ratios) as in Cosmetic sheet B-1. At this time, the inks were applied without movement of the polylactic acid sheet such that ink droplets of different colors overlapped at each spot. The sheet after the printing was dried in an environment at 50° C., to obtain Cosmetic sheet B-2 (Reference Example).

Figure 3:
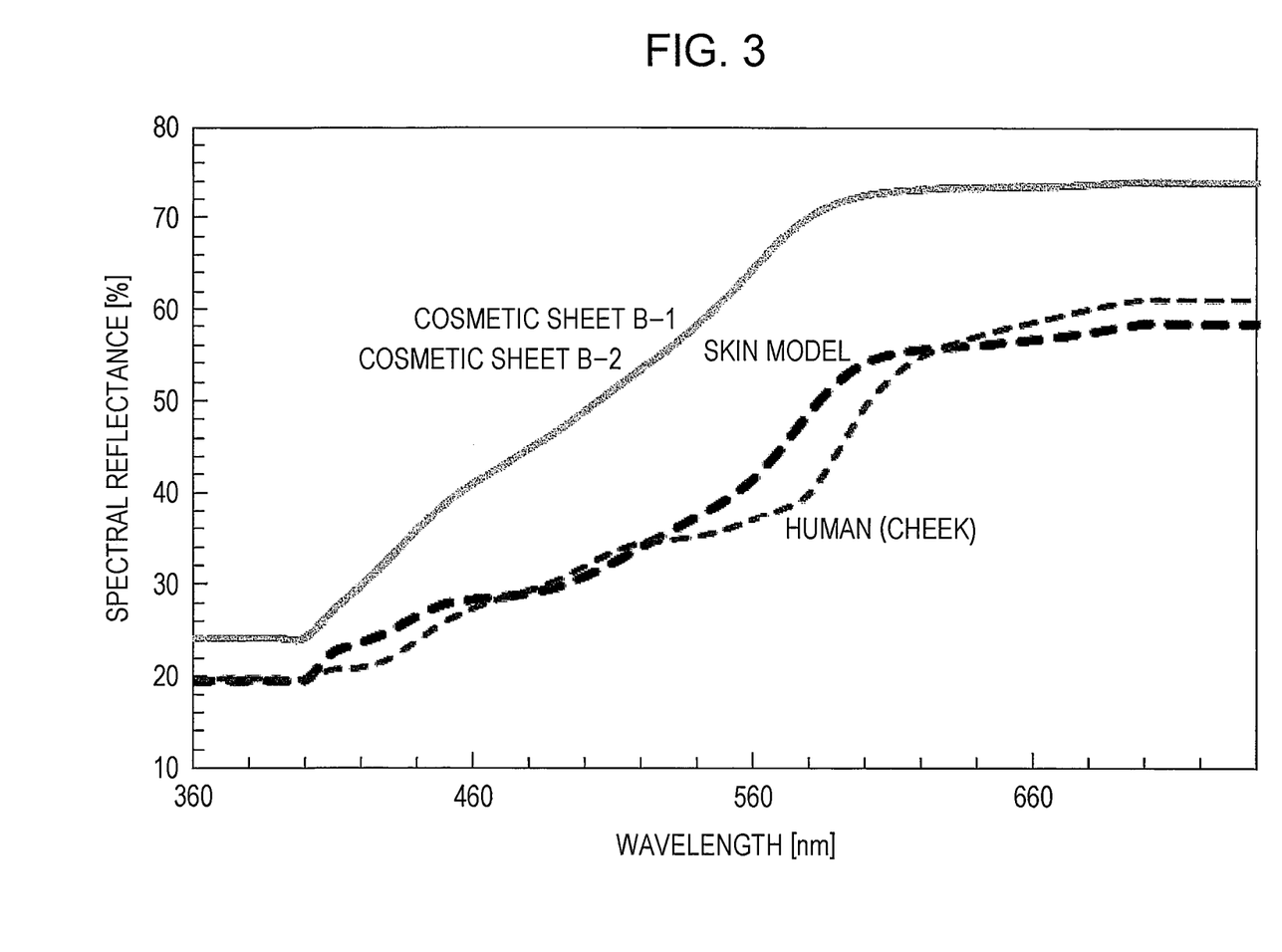
FIG. 3 is a graph of a spectral reflectance curve of Cosmetic sheet B-1 produced by a method for producing a cosmetic sheet according to an embodiment of the present disclosure, and a spectral reflectance curve of Cosmetic sheet B-2 produced by a different method.

Cosmetic sheets B-1 and B-2 were measured in terms of spectral reflectances in wavelengths of 360 nm to 740 nm using a spectrophotometer (such as CM-700d manufactured by KONICA MINOLTA JAPAN, INC.) with a main light source of D50 and a measurement mode of SCE. The results are illustrated in FIG. 3. As is clear from FIG. 3, in Cosmetic sheet B-1 and Cosmetic sheet B-2, the spectral reflectances completely overlap. These coating films each had a spectral reflectance curve having, in the wavelength region of 550 nm or more and 610 nm or less, a first inflection point, and, in the wavelength region of less than 550 nm, a second inflection point. In addition, in each of these coating films, the spectral reflectance at the first inflection point was higher than the spectral reflectance at the second inflection point. In addition, in each of these coating films, spectral reflectances throughout the wavelength region of more than 580 nm were equal to or higher than the spectral reflectance at a wavelength of 580 nm. The color difference of each of these coating films having such spectral reflectances from the skin model was visually evaluated, and found to be small.

On the other hand, the masking capability of Cosmetic sheet B-1 and Cosmetic sheet B-2 being placed over a blotch model was subjected to a sensory evaluation. Specifically, Cosmetic sheet B-1 and Cosmetic sheet B-2 were placed over a blotch model, and six assessors visually judged which cosmetic sheet had a higher capability of masking the blotch. As a result, six assessors out of six said that Cosmetic sheet B-1 exhibited a higher capability of masking the blotch.

Figure 4A:
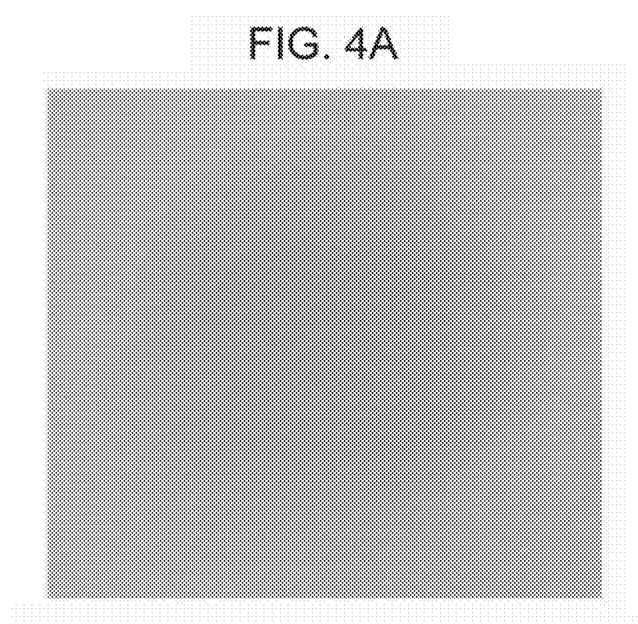
FIG. 4A is a photograph of Cosmetic sheet B-1 produced by a method for producing a cosmetic sheet according to an embodiment of the present disclosure, the Cosmetic sheet B-1 being placed over a blotch model.
Figure 4B:
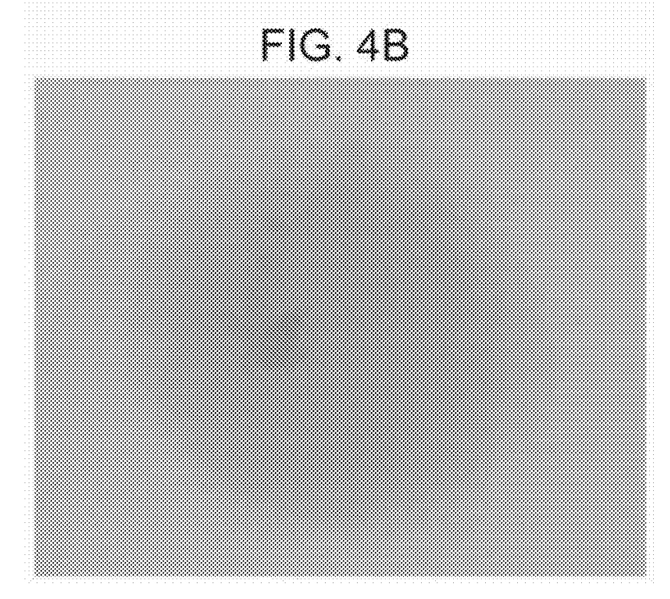
FIG. 4B is a photograph of Cosmetic sheet B-2 produced by a different method, the Cosmetic sheet B-2 being placed over a blotch model.
Figure 5A:
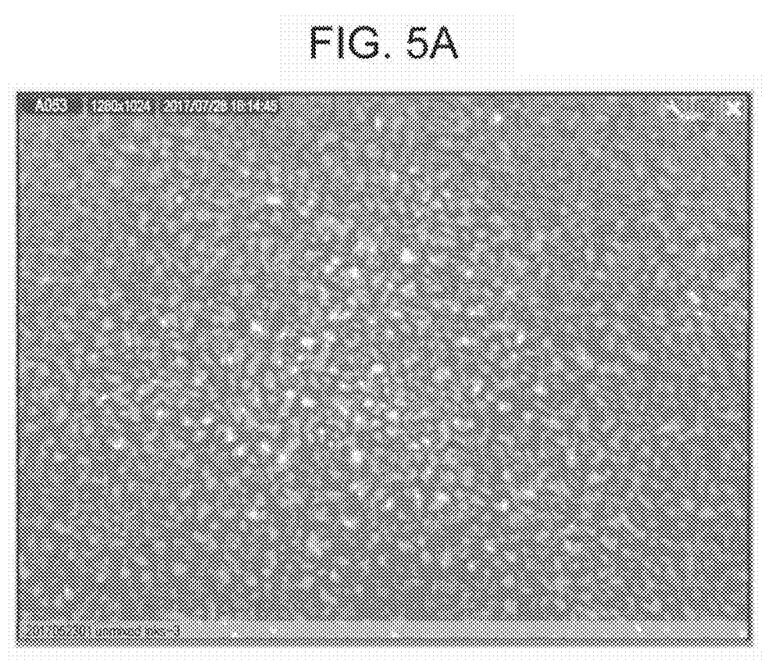
FIG. 5A is an enlarged photograph of the surface of Cosmetic sheet B-1 produced by a method for producing a cosmetic sheet according to an embodiment of the present disclosure.
Figure 5B:
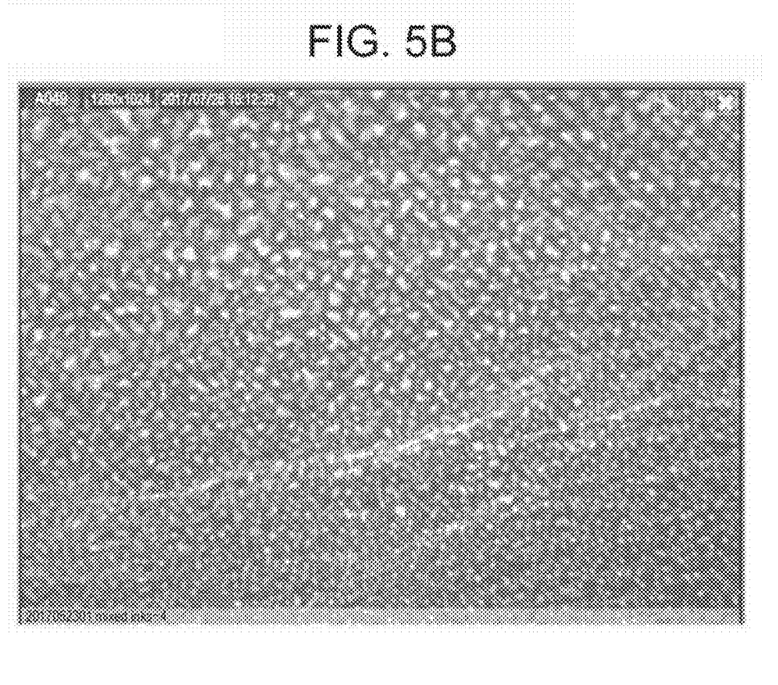
FIG. 5B is an enlarged photograph of the surface of Cosmetic sheet B-2 produced by a different method.

Images of Cosmetic sheet B-1 and Cosmetic sheet B-2 placed over the blotch model are respectively illustrated in FIG. 4A and FIG. 4B. Microscopically enlarged photographs of Cosmetic sheets B-1 and B-2 are respectively illustrated in FIG. 5A and FIG. 5B. As is clear from the enlarged photographs in FIG. 5A and FIG. 5B, in Cosmetic sheet B-1, pigments of different colors are arranged so as to be displaced from each other on the surface of the sheet, compared with Cosmetic sheet B-2. For this reason, regions to which pigments did not adhere had a small area, which inferentially resulted in a high masking capability. In particular, spots to which the white-ink-derived white-based colorant alone adhered tended to exhibit a light scattering effect, which inferentially made the color of the blotch model less noticeable.

INDUSTRIAL APPLICABILITY

A cosmetic ink according to an embodiment of the present disclosure enables, irrespective of the amount of the ink applied, reproduction of a color close to the color of the skin. A method for producing a cosmetic sheet according to an embodiment of the present disclosure provides a cosmetic sheet that masks a blotch and the like and enables reproduction of a color close to the color of the skin.

What is claimed is:

1. A cosmetic film comprising:
   a thin film of a thickness of 10 nm or more and 1000 nm or less, and
   a cosmetic ink printing on the thin film,
   the cosmetic ink including:
   (A) a plurality of colorants selected from the combination of at least a white-based colorant, a red-based colorant, a yellow-based colorant, and a blue-based colorant, wherein the mass ratio of the blue-based colorant content to the total amount of (A) colorant is 0.25 or more and 1.0 or less;
   (B) a higher alcohol having 3 or more carbon atoms;
   (C) purified water;
   (D) an acrylic-based resin including a copolymer of two or more acrylic-based monomer species, the acrylic-based resin being present in an amount of 0.1 mass % or more and 10 mass % or less of the cosmetic ink; and
   (E) a film-forming agent being at least one selected from the group consisting of acrylic-based polymers, polysaccharide-based polymers, sugar alcohol, sterols, esters, and modified corn starch, the film-forming agent present in an amount of 0.3 to 20 parts by mass of the cosmetic ink,
   wherein a spectral reflectance curve obtained by measuring spectral reflectances in wavelengths of 400 nm to 700 nm of a coating film of the cosmetic ink has a first inflection point in a wavelength region of 550 nm or more and 610 nm or less, and a second inflection point in a wavelength region of less than 550 nm,
   a spectral reflectance at the first inflection point is higher than a spectral reflectance at the second inflection point, and
   spectral reflectances throughout a wavelength region of more than 580 nm are equal to or higher than a spectral reflectance at a wavelength of 580 nm.

2. The cosmetic film according to claim 1, wherein the coating film of the cosmetic ink has an $L^*$ value of 48 or more in the $L^*a^*b^*$ color system.

3. The cosmetic film according to claim 1, wherein the (E) film-forming agent has an HLB value of 8 to 19.

4. The cosmetic film according to claim 1, wherein the (E) film-forming agent includes an acrylic-based polymer.

5. The cosmetic film according to claim 1, wherein the (A) colorant includes a black-based pigment or a black-based dye.

6. The cosmetic film according to claim 1, wherein the (A) colorant has an average particle size of 2 μm or less.

7. The cosmetic film according to claim 1, the cosmetic ink having a viscosity at 25° C. of 50 mPa·s or less measured with a cone-plate viscometer at a shear rate of 1000 (1/s).

8. The cosmetic film according to claim 1, the cosmetic ink having a pH of 6 to 10.

9. The cosmetic film according to claim 1, the cosmetic ink having a surface tension of 50 mN/m or less.

10. An ink jet printing ink comprising a cosmetic ink including:
    (A) a plurality of colorants selected from the combination of at least a white-based colorant, a red-based colorant, a yellow-based colorant, and a blue-based colorant, wherein the mass ratio of the blue-based colorant content to the total amount of (A) colorant is 0.25 or more and 1.0 or less
    (B) a higher alcohol having 3 or more carbon atoms;
    (C) purified water;
    (D) an acrylic-based resin including a copolymer of two or more acrylic-based monomer species, the acrylic-based resin being present in an amount of 0.1 mass % or more and 10 mass % or less of the cosmetic ink; and
    (E) a film-forming agent being at least one selected from the group consisting of acrylic-based polymers, polysaccharide-based polymers, sugar alcohol, sterols, esters, and modified corn starch, the film-forming agent present in an amount of 0.3 to 20 parts by mass of the cosmetic ink,
    wherein a spectral reflectance curve obtained by measuring spectral reflectances in wavelengths of 400 nm to 700 nm of a coating film of the cosmetic ink has a first inflection point in a wavelength region of 550 nm or more and 610 nm or less, and a second inflection point in a wavelength region of less than 550 nm,
    a spectral reflectance at the first inflection point is higher than a spectral reflectance at the second inflection point, and
    spectral reflectances throughout a wavelength region of more than 580 nm are equal to or higher than a spectral reflectance at a wavelength of 580 nm.

11. An ink cartridge comprising a cosmetic ink including:
    (A) a plurality of colorants selected from the combination of at least a white-based colorant, a red-based colorant, a yellow-based colorant, and a blue-based colorant, wherein the mass ratio of the blue-based colorant content to the total amount of (A) colorant is 0.25 or more and 1.0 or less;
(B) a higher alcohol having 3 or more carbon atoms;
(C) purified water;
(D) an acrylic-based resin including a copolymer of two or more acrylic-based monomer species, the acrylic-based resin being present in an amount of 0.1 mass % or more and 10 mass % or less of the cosmetic ink; and
(E) a film-forming agent being at least one selected from the group consisting of acrylic-based polymers, polysaccharide-based polymers, sugar alcohol, sterols, esters, and modified corn starch, the film-forming agent present in an amount of 0.3 to 20 parts by mass of the cosmetic ink,
wherein a spectral reflectance curve obtained by measuring spectral reflectances in wavelengths of 400 nm to 700 nm of a coating film of the cosmetic ink has a first inflection point in a wavelength region of 550 nm or more and 610 nm or less, and a second inflection point in a wavelength region of less than 550 nm,
a spectral reflectance at the first inflection point is higher than a spectral reflectance at the second inflection point, and
spectral reflectances throughout a wavelength region of more than 580 nm are equal to or higher than a spectral reflectance at a wavelength of 580 nm.

12. The cosmetic ink film according to claim 1, wherein the thin film is composed of biocompatible materials and is thereby suitable to be directly or indirectly, affixed or adhered to skin.

* * * * *